US011229431B2

(12) United States Patent
Ockell et al.

(10) Patent No.: US 11,229,431 B2
(45) Date of Patent: Jan. 25, 2022

(54) WOUND CLOSURE DEVICE

(71) Applicant: GOTHENBURG MEDTECH INNOVATIONS AB, Kungälv (SE)

(72) Inventors: Jonas Ockell, Kungälv (SE); Magnus Ojde, Kungälv (SE)

(73) Assignee: GOTHENBURG MEDTECH INNOVATIONS AB, Kungälv (SE)

( * ) Notice: Subject to any disclaimer, the term of this patent is extended or adjusted under 35 U.S.C. 154(b) by 289 days.

(21) Appl. No.: 16/603,222

(22) PCT Filed: Apr. 23, 2018

(86) PCT No.: PCT/EP2018/060372
§ 371 (c)(1),
(2) Date: Oct. 5, 2019

(87) PCT Pub. No.: WO2018/193136
PCT Pub. Date: Oct. 25, 2018

(65) Prior Publication Data
US 2020/0029956 A1 Jan. 30, 2020

(30) Foreign Application Priority Data

Apr. 21, 2017 (EP) ..................... 17167459

(51) Int. Cl.
*A61B 17/04* (2006.01)
*A61B 17/00* (2006.01)
(52) U.S. Cl.
CPC ...... *A61B 17/0482* (2013.01); *A61B 17/0487* (2013.01); *A61B 2017/00818* (2013.01);
(Continued)

(58) Field of Classification Search
CPC ............ A61B 17/0482; A61B 17/0487; A61B 2017/00818; A61B 2017/0488;
(Continued)

(56) References Cited

U.S. PATENT DOCUMENTS 5,242,457 A * 9/1993 Akopov ............... A61B 17/064
227/175.1
8,056,789 B1 11/2011 White et al.
(Continued)

FOREIGN PATENT DOCUMENTS

EP 2248474 A2 11/2010
EP 3000407 A2 3/2016
(Continued)

OTHER PUBLICATIONS

International Search Report (dated Aug. 2, 2018) for corresponding International App. PCT/EP2018/060372.

*Primary Examiner* — Julian W Woo
(74) *Attorney, Agent, or Firm* — WRB-IP LLP

(57) ABSTRACT

A wound closure device for closing a surgical wound in a tissue, wherein the wound closure device includes a first jaw, a second jaw and a handle. The first jaw is arranged for receiving a first cartridge including a plurality of slots for holding wound closers and wherein the second jaw is provided with a plurality of tracks. The plurality of tracks guide a respective one of the male ends and a respective one of the female ends towards each other and to an interlocked state where the respective one of the male ends and the respective one of the female ends are interlocked with each other.

16 Claims, 9 Drawing Sheets

(52) U.S. Cl.
CPC ............... *A61B 2017/0488* (2013.01); *A61B 2017/0496* (2013.01)

(58) Field of Classification Search
CPC .... A61B 2017/0496; A61B 2017/0461; A61B 2017/0472; A61B 2017/0479; A61B 2017/06057; A61B 2017/06171; A61B 2017/06176; A61B 2017/07257; A61B 2017/07271; A61B 2017/07278; A61B 17/0644; A61B 17/07207; A61B 17/062; A61B 17/06166; A61B 17/0467; A61B 17/04

See application file for complete search history.

(56) References Cited

U.S. PATENT DOCUMENTS

| | | | | |
|---|---|---|---|---|
| 8,313,509 | B2* | 11/2012 | Kostrzewski | A61B 17/0487 606/232 |
| 8,590,762 | B2* | 11/2013 | Hess | A61B 17/0682 227/176.1 |
| 9,307,989 | B2* | 4/2016 | Shelton, IV | A61B 17/0643 |
| 2003/0125734 | A1 | 7/2003 | Mollenauer | |
| 2014/0058417 | A1 | 2/2014 | Levy et al. | |

FOREIGN PATENT DOCUMENTS

| | | | |
|---|---|---|---|
| WO | 2011068533 A1 | 6/2011 | |
| WO | 2012141679 A1 | 10/2012 | |

\* cited by examiner

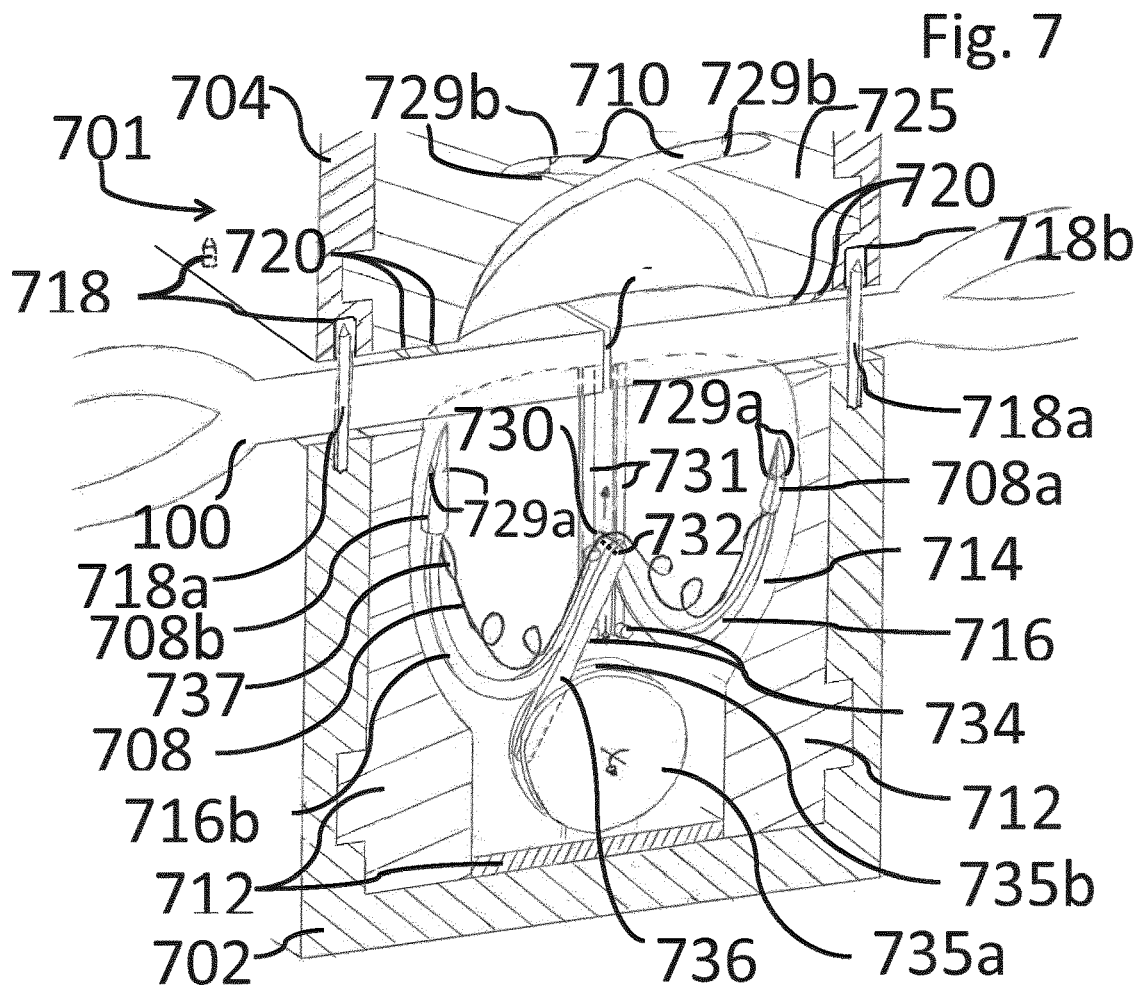
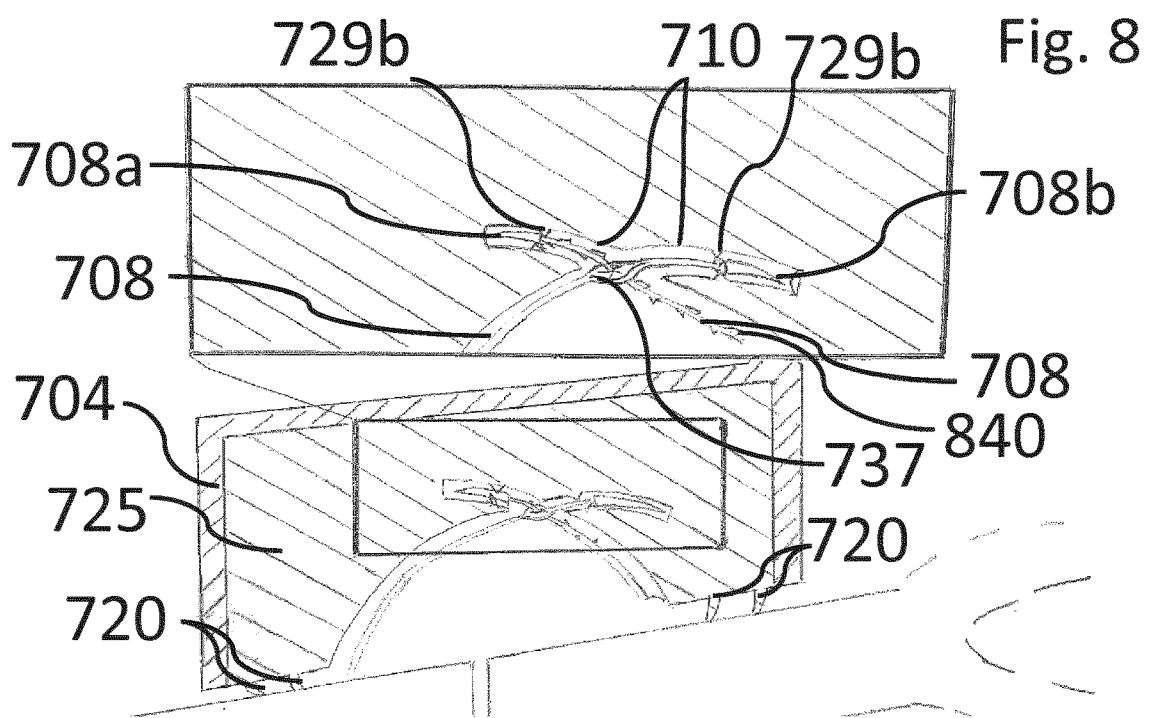

Fig. 9
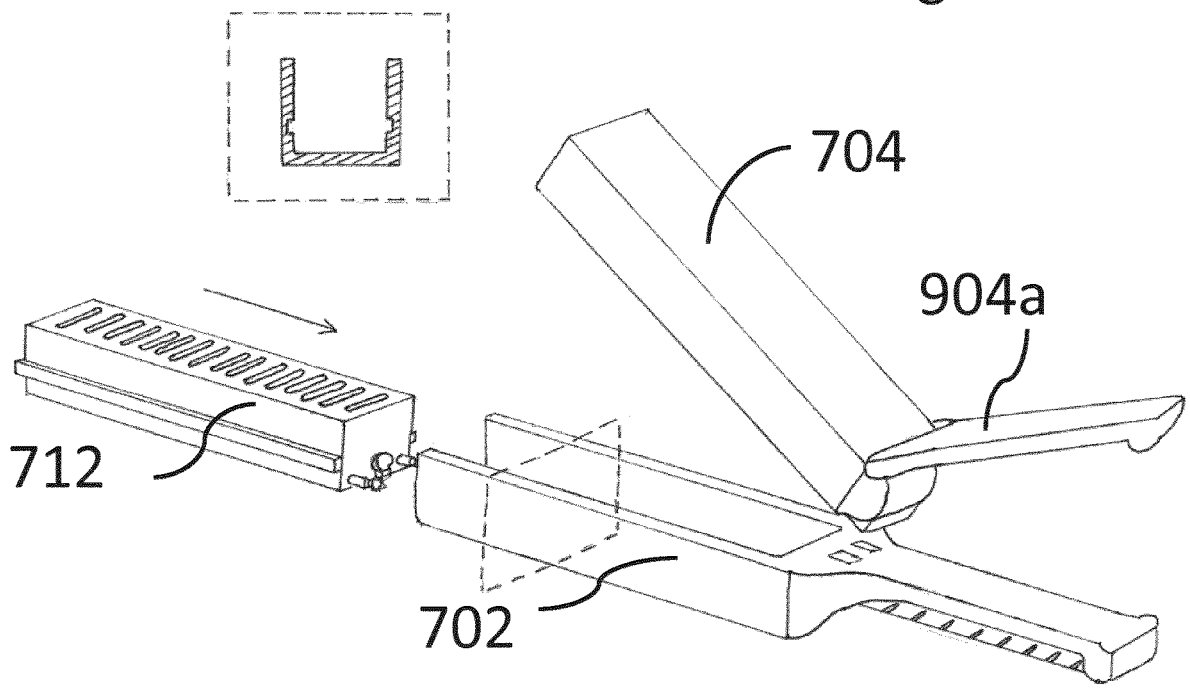
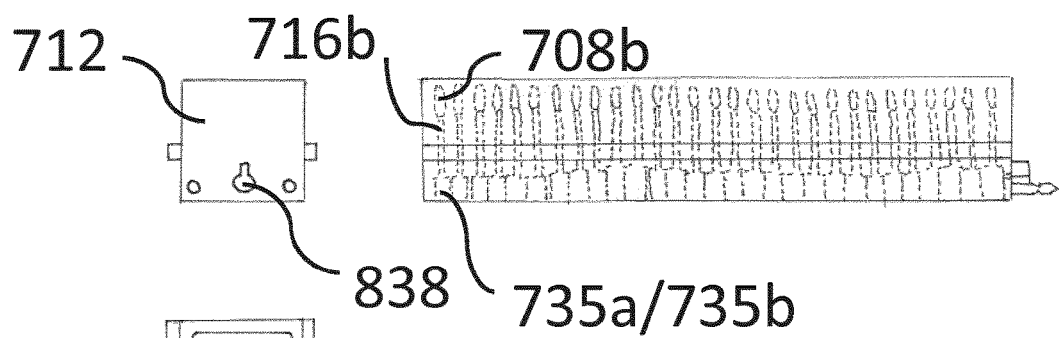
Fig. 10
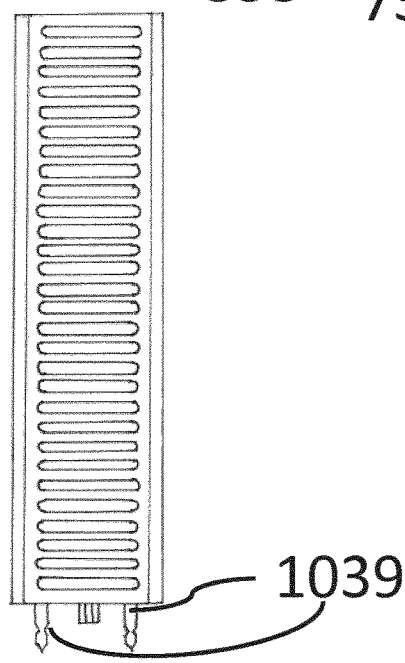

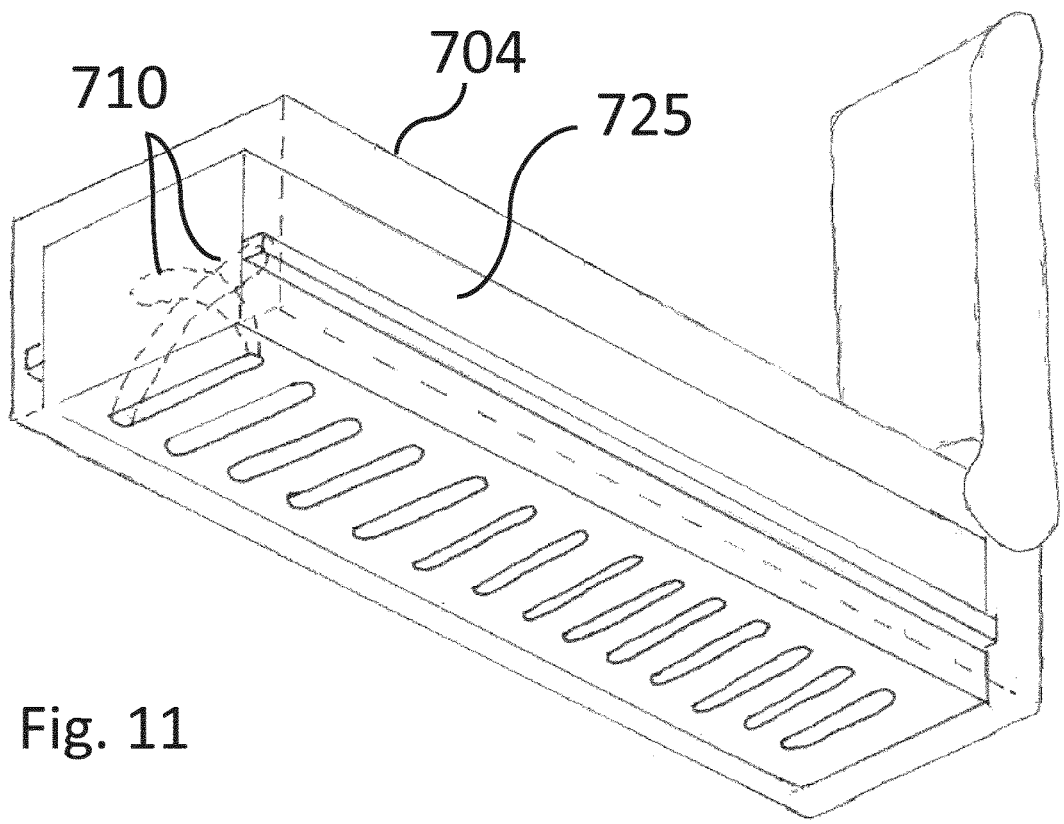
Fig. 11
Fig. 12
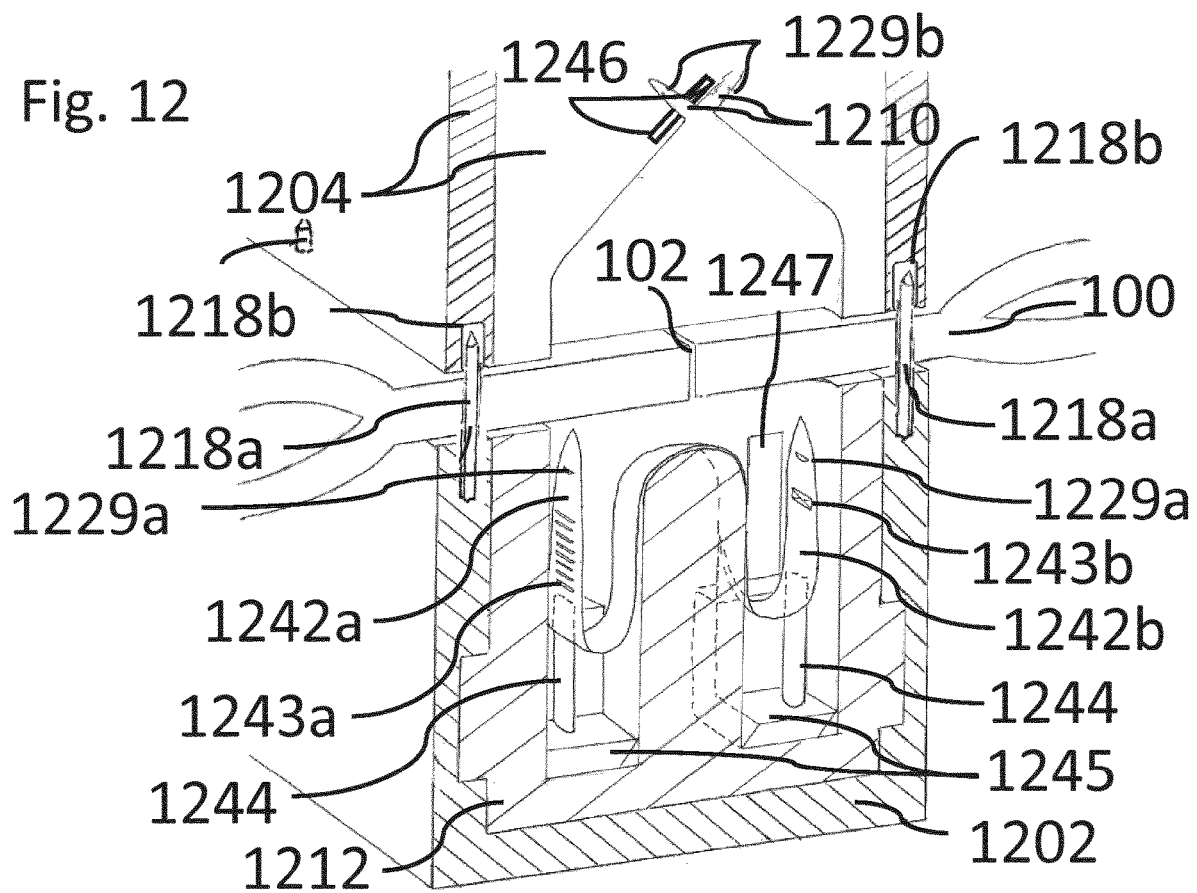

WOUND CLOSURE DEVICE

BACKGROUND AND SUMMARY

The present invention relates to a wound closure device, a cartridge, a method for closing a wound and a kit of parts which when mounted forms a wound closure device.

To this date, the recommended technique for closing the muscle fascia and/or other tissue in a surgical wound is to manually suture the wound by use of needle and thread operated using a needle holder.

When closing the muscle fascia after a midline incision, for instance, it is important that the suturing is done thoroughly, as the quality of the sutured wound is dependent, among other things, of the positions of, as well distance between, the suture bites. This technique is time consuming but a properly done suturing of the muscle fascia significantly reduces the risk of wound rupture as well as later occurring incisional hernias. This has been described in numerous studies, for instance M van 't Riet et al (Meta-analysis of techniques for closure of midline abdominal incisions, British Journal of Surgery 2002, 89, 1350±1356) and in the recommendations from the European Hernia Society (European Hernia Society guidelines on the closure of abdominal wall incisions, Hernia, 2015 February; 19(1): 1-24. doi: 10.1007/s10029-014-1342-5).

In summary, the golden standard for closing an abdominal midline incision is suturing with an absorbable suture according to well-substantiated guidelines regarding the size of suture bites as well as the distance between the bites. Also, as described above, this is a time consuming process, and, since it is also well-substantiated that increased time in surgery increases the risk of various complications, it is desired to be able to close a surgical wound, particularly the muscle fascia of an abdominal surgical wound, in a more efficient way without compromising the quality of the closure.

It is desirable to improve the current state of the art and to mitigate at least some of the above mentioned problems.

According to a first aspect of the invention a wound closure device for closing a surgical wound in a tissue is provided. The wound closure device comprises a first jaw, a second jaw and a handle;

wherein said first jaw is arranged for receiving a first cartridge, and wherein said first jaw is provided with said first cartridge, wherein said first cartridge comprises a plurality of slots holding wound closers, said slots being distributed along a longitudinal extension of said first cartridge, and wherein each of said plurality of wound closers comprise a male and female end;

wherein said second jaw is provided with a plurality of tracks;

wherein said tracks are curved and/or linear and wherein said tracks crosses each other;

wherein said first and second jaws are adapted to be arranged on a respective side of the tissue;

wherein upon one actuation of said handle said first jaw forces said male ends and said female ends to exit said first cartridge, to penetrate said tissue on a respective side of said surgical wound and to enter a respective one of said plurality of tracks, wherein said plurality of tracks are arranged to receive said male and female ends and to guide a respective one of said male ends and a respective one of said female ends towards each other and to an interlocked state where said respective one of said male ends and said respective one of said female ends are interlocked with each other or wherein upon one actuation of said handle said first jaw forces said male ends to exit said first cartridge, to penetrate said tissue on one side of said surgical wound, to enter a respective one of said plurality of tracks, to exit said second jaw, to penetrate the tissue on the opposite side of said surgical wound and to enter said first cartridge; and wherein said plurality of tracks are arranged to receive said male ends and to guide said male to the tissue on said opposite side of said surgical wound; and wherein said first cartridge is arranged to receive said male ends after it has passed said tissue and to guide said male ends to a respective one of said female ends and into an interlocked state where said one of said male ends and one of said female ends are interlocked with each other.

According to one aspect of the present invention a kit of parts is provided. The kit of parts comprises:

a first part comprising a first handle portion and a first jaw;

a second part comprising a second jaw;

a third part comprising a first cartridge;

a fourth part comprising a second cartridge;

wherein said first and second parts each comprises cooperating fastening means for locking the first and second jaws to each other;

wherein said first jaw is arranged for receiving the first cartridge comprising a plurality of slots for holding wound closers along a longitudinal extension of said first jaw, wherein each of said plurality of wound closers comprise a male and female end, and wherein said first jaw comprises exit openings for said male ends and said female ends of said wound closure;

wherein said second jaw is arranged for receiving the second cartridge that comprises a plurality of tracks;

wherein said first and second jaws are adapted to be arranged on, a respective side of the tissue; and wherein upon one actuation of said handle portion said first jaw forces said male ends and said female ends to exit through a respective opening in said first jaw, to penetrate said tissue on a respective side of a surgical wound and to enter a respective one of said plurality of tracks in said second cartridge, wherein said plurality of tracks in said second cartridge are arranged to receive said male and female ends and to guide a respective one of said male ends and a respective one of said female ends towards each other and to an interlocked state where said respective one of said male ends and said respective one of said female ends are interlocked with each other, wherein the first and second part when mounted using the cooperating fastening means forms a wound closure device arranged for receiving a first and a second cartridge.

In the above, a kit of part comprising a first and a second cartridge has been described. Alternatively, the kit of parts may comprise a device configured to receive only a first cartridge, wherein the tracks are formed in the second jaw, as described in relation to the first aspect of the invention.

According to a second aspect of the present invention, a cartridge for use with a wound closure device for closing a surgical wound in a tissue is provided, wherein said cartridge comprises connection means for connecting said cartridge to a wound closure device and power receiving means configured to receive power from said power transfer means of said wound closure device, a plurality of slots holding wound closers, said slots being distributed along a longitudinal extension of said first cartridge, and wherein each of said plurality of wound closers comprise a male and female end, and actuation means operatively coupled to said power receiving means and configured to force said male ends and said female ends to exit said first cartridge and to penetrate said tissue on a respective side of said surgical wound.

Embodiments of the above aspects of the invention are described below. Effects and features of these aspects of the inventive concept are largely analogous.

The essence of the present invention is to provide a wound closure device that applies a plurality of wound closers, e.g. sutures, in one actuation, which wound closers preferably are self-locking. This provides a rapid and secure way to close a surgical wound and at the same time ensuring the quality of the closure. The use of a wound closure device as described here in would without a doubt be an efficient way to save money worldwide, since operating time would be significantly reduced.

According to one example and as known in the art, the suture is strong enough to hold the tissue together and yet smooth and tissue-friendly enough to minimize the risk of unwanted bowel adhesion to the inside of the muscle fascia after suturing, (increasing the risk of subsequent bowel obstruction), that may occur due to inflammation caused by a foreign body reaction. Using sutures, the amount of foreign material left in the wound is minimized and, since the suture type often recommended for closing e.g. an abdominal midline incision is typically resorbable, (i.e. it is eventually absorbed by the body), all foreign material ultimately disappears. A minimal amount of resorbable material is beneficial for the same reasons as described above. Together, this constitutes some of the reasons that suturing is preferred before e.g. staples or other non-resorbable or resorbable materials, that due to a harder composition and/or more foreign material, might cause adverse effects on the wound healing process and increase the risk of complications, as described above.

In the following, the second jaw being provided with a plurality of tracks is to be understood as meaning that the second jaw has a plurality of tracks integrally formed with the jaw, e.g. a plurality of tracks formed by means of molding or milling of the second jaw. Alternatively, the second jaw being provided with a plurality of tracks may be understood as meaning that the tracks are formed in a removable cartridge that is to be held by the second jaw, i.e. a plurality of tracks integrally formed with the cartridge, e.g. a plurality of tracks formed by means of molding or milling of the cartridge.

According to at least one example embodiment of the invention, the tissue is muscle fascia. Hence, the wound closure device may be used to close the muscle fascia of the surgical wound.

According to at least one example embodiment of the invention, the wound closure device may be used to close the muscle fascia divided during a surgical midline incision of the abdomen.

According to at least one example embodiment of the invention, the wound closers penetrates the tissue simultaneously or subsequently upon one single actuation. In other words, the single actuation may cause the wound closers to penetrate the tissue at the same time or the single actuation may cause the wound closers to penetrate the tissue in a sequence after each other. When penetrating the tissue in a sequence after each other the force which is applied on the tissue while the wound closers are penetrating the tissue is spread over the tissue and over time.

In other words, at a single actuation of the handle more than one wound closer, e.g. at least 5 or 10 or 15 or 20 wound closures, will penetrate the tissue and be forced into the interlocked state. Hence, there is no need for one actuation per wound closer, but more than one actuation might be needed for closing the whole wound—according to one example the wound closing device is moved between two actuations, alternatively or additionally the wound actuation device is not moved between two actuations, but the first actuation (a single actuation) operates on, a first group/set of wound closing devices and the next actuation (a single actuation) operates on a another group/set of wound closing devices different from said first group/set of wound closing devices.

According to at least one example embodiment of the invention the single actuation is a movement of the handle along a path; according to one example the movement of the handle starts at a starting position and ends when the handle has reached an end position different from the starting position at which end position the interlocking of the closures have been achieved; according to another example the handle starts at a starting position and passes said end position and thereafter returns to the starting position. The path may be linear or curved, or a combination of the two. The linear path may e.g. be parallel, or transverse to the longest extension of the first and/or the second jaw, and curved path may have any shape and e.g. be circular or partly circular or elliptical, or partly elliptical. Additionally, or alternatively, the direction in which the handle is moved may be in the continuation of the longest extension of the first and/or the second jaw. The direction of the path may be predetermined, i.e. the same or substantially the same for each single actuations of the handle, or it may be controlled by the person operating the handle so the path of the handle may be varied between different single actuations of the handle depending on the situation at hand.

According to at least one example embodiment of the invention the handle may pulled or pushed in respect to other parts of the wound closure device. For example, the single actuation may be pulling the handle along the first and/or second jaw.

According to at least one example embodiment of the invention, the single actuation may comprise one or several sub-actuations. For example, one sub-actuation may cause the male ends to penetrate the tissue on one side of the surgical wound and another sub-actuation may cause the female ends to penetrate the tissue on the other side of the wound. Additionally, or alternatively, a first sub-actuation may cause the first and second jaws to physically contact the tissue on a respective side of the tissue whereas a second or later sub-actuation may cause the wound closers to penetrate the tissue. The moving direction of the handle may be same or different for all sub-actuation.

According to at least one example embodiment of the invention, said first jaw is fixedly attached or removably attached to said head and wherein said second jaw is fixedly attached or removably attached to said head.

According to at least one example embodiment of the invention said first and second jaw is arranged in said first state by attaching said first handle portion to said second handle portion.

According to at least one example embodiment of the invention the jaws may be straight or they may be curved or slightly curved.

According to at least one example embodiment of the invention at least one of the jaws may comprise an arched leading portion. The arched leading portion being the end of the jaw arranged furthest away from the handle or handle portion(s). The arched leading portion facilitates the positioning of the jaw prior to closing the surgical wound.

According to at least one example embodiment of the invention, tracks of the second jaw may be curved such that they may cross each other. According to at least one example embodiment of the invention the tracks may start in a straight manner and then curve at the end such that they cross each other.

According to at least one example embodiment of the invention the distance between the first and the second jaw may be adjustable. This allows for using the wound closure device on tissue, e.g. muscle fascia, of different thickness. In at least one example embodiment of the invention the distance between the first and the second jaws is adjustable when the first and the second jaws are mounted together, e.g. the cooperating fastening means may provide several states at which the first and the second jaws may be mounted together, where the different states provides different distances between the jaws. The first and the second jaw may be provided on a respective side of the tissue when separated from each other, and then mounted together at a distance which is adjusted to the tissue which should be closed, e.g. the distance may be adjusted in such way that the jaws are provided in physical contact with the tissue.

According to at least one example embodiment of the invention, the wound closure devices father comprises one or several combs, or comb-like structure, arranges in the first jaw wherein said comb(s) comprises, comprise teeth arranged to push the male and/or the female end through the tissue upon said one actuation of the handle.

According to at least one example embodiment of the invention the teeth may be metallic or they may be made from a plastic material, or any other material currently in use in surgery. The teeth may for be straight or curved and they may moreover be rigid or flexible.

According to at least one example embodiment, the wound closure device further comprises power transfer means operatively coupled to one actuation of said handle, for transferring power to said first cartridge.

According to at least one example embodiment, the wound closure device further comprises power transfer means operatively coupled to one actuation of said handle, for transferring power to said first cartridge and from said first cartridge to at least one of said wound closers held in said first cartridge.

According to at least one example embodiment, the tracks are formed in said second jaw.

According to at least one example embodiment, the second jaw is provided with a second cartridge, and wherein said tracks are formed in said second cartridge.

According to at least one example embodiment of the invention, said handle comprises two handle portions wherein at least one of said handle portions is an actuating portion.

According to at least one example embodiment of the invention, the handle comprises a first handle portion and a second handle portion wherein one or both of the first and the second handle portion is/are the actuating portion. The actuation portion is connected to the first cartridge comprising the wound closers in such way that a motion of the actuation portion induces the wound closers to penetrate the tissue and thereafter reach the interconnected state. In one example embodiment, this is done by means of the wound closure device being provided with power transfer means for transferring power to the first cartridge and the first cartridge being provided with power receiving means for receiving said transferred power.

According to at least one example embodiment of the invention, the actuating portion may be a movable portion whereas any other portion of the handle may be a fixed portion. For example, the user of the wound closure device may hold the two handle portions in one hand and may push the actuation portion towards the other portion e.g. in a direction transverse to the direction of the longest extension of the first and/or the second jaw. In at least another embodiment of the invention, both handle portions are movable portions but moving the other portion does not induce the wound closers to penetrate the tissue. For example, the distance between the first and the second jaws may be adjustable by moving both the first and second handle portions towards each other, e.g. the wound closure device may be scissor-like and, the distance between the first and the second jaws may be adjustable by moving two handle portions towards each other. According to at least one example embodiment of the invention the actuating portion may be a knob which may be rotated in order to induce the wound closers to penetrate the tissue.

According to at least one example embodiment of the invention, said first jaw is configured to be arranged underneath or on the internal side of the tissue and wherein said second jaw is configured to be arranged above or on the external side of said tissue. In other words, in use, the first jaw is arranged in contact with or in proximity to the surface of the tissue which is facing the inside of the body and the second jaw is arranged in contact with or in proximity to the surface of the tissue which is facing the surroundings.

According to at least one example embodiment of the invention, the interlocked state is such that the ends that are interlocked with each other are a male end and a female end of the same wound closer, or a male and a female end of two adjacent wound closers.

According to at least one example embodiment of the invention an interrupted suture is formed when a male end and a female end of the same wound closure is interlocked with each other.

According to at least one example embodiment of the invention a continuous suture is formed when a male end and a female end of two adjacent wound closures are interlocked with each other.

According to at least one example embodiment of the invention, the c-c distance between two adjacent slots is 1-10 mm along the longitudinal extension of said first jaw. The distance between two adjacent slots determines the distance between two adjacent wound closers. A small distance reduces the risk of wound rupture as well as later occurring incisional hernias.

According to at least one example embodiment of the invention, said plurality of wound closers are adjustable, partly flexible, self-locking, and/or self-penetrating.

According to at least one example embodiment of the invention, said male end of each wound closer comprises one or several protrusions and said female end of each wound closer comprises an opening configured for receiving said male end and wherein said protrusions of said male end are configured to prevent the male end from sliding out of the female end when in said interlocked state.

According to at least one example embodiment the suture may for example comprise beads or grooves filling the same functions as those present on a beaded or flat locking strap preventing the male end from sliding out of the female end. The suture may for example be a beaded strap or a flat strap.

According to at least one example embodiment of the invention the suture may comprise one or more anchors arranged on at least the part of the suture closest to the male end. The anchors may be flexible anchors which are adapted to allow sliding in to the female end, e.g. the flexible anchors are pressed towards the suture while sliding into the female end. After sliding through the suture the flexible anchors will go back towards its normal unbiased state which prevents the male end to slide out from the female end.

According to at least one example embodiment of the invention, the suture may be a monofilament suture or it may be a multi-filament suture; e.g. a braided suture.

According to at least one example embodiment of the invention, the suture may be an absorbable suture or a non-absorbable suture.

According to at least one example embodiment of the invention, the suture may be double-armed. Hence, both the male and the female end comprise a needle which is pushed through the tissue upon the single actuation of the handle. An opening in the female end may be arranged before the needle, as seen from the middle of the suture towards the female end of the suture.

According to at least one example embodiment of the invention, the suture may be single-armed. In this case, the needle of the male end is pushed through the tissue by a curved comb in such a way that the needle is first pushed through the tissue on one side of the wound, passes through the cartridge of the other side and then through the tissue of the other side of the wound from the opposite direction. The needle of the male end thus returns to the first cartridge and is interlocked with the female lock member.

According to at least one example embodiment of the invention, said tracks of said second jaw are arch-formed and said tracks crosses each other. It shall be understood that arch-formed means that the tracks a curved to form a part of an ellipse.

According to at least one exemplary embodiment of the invention, said tracks are formed in said second jaw.

According to at least one exemplary embodiment of the invention, said second jaw is provided with a second cartridge, and said tracks are formed in said second cartridge.

According to at least one example embodiment of the present invention, said first cartridge and/or said second cartridge is/are single-use and/or disposable.

According to at least one example embodiment of the invention, said tracks are configured to guide said male and female end such that said male end enters through the opening of said female end where said tracks cross each other. The male end will be guided through the opening of the female end where the tracks cross each other.

According to at least one example embodiment of the invention, said first and/or said second jaw further comprises at least one fastening pin for partially or fully penetrating the tissue wherein the height of said at least one fastening pin is 1-15 mm. The fastening pin(s) is/are used to position the tissue between the first and the second jaw prior closing the wound. For example, the fastening pins may be used to provide the tissue on the two sides in close proximity to each other in a way such that the tissue do not move when actuating the handle.

According to at least one example embodiment of the invention the height of the at least one fastening pin is at least 1 mm, or at least 3 mm, or at least 5 mm. Additionally, or alternatively, the height of the at least one fastening pin may be less than 15 mm, or less than 12 mm or less than 10 mm, or less than 7 mm. For example, the height of the at least one fastening pin may be in the range of 1-15 mm, or 1-12 mm, or 3-10 mm, or any height in between those ranges.

According to at least one example embodiment of the invention, the length of the first and/or the second jaw is 20-160 mm, or 40-140 mm, or 50-130 mm.

According to at least one example embodiment of the invention, the distance between a male end and a female end of the same wound closure when mounted in said first cartridge is 3-35 mm, 3-25 mm, or 5-20 mm and for example 32 mm.

According to at least one example embodiment of the invention, the length of the first and/or second jaw may be at least 20 mm, or at least 30 mm, or at least 40 mm, or at least 50 mm. Additionally, or alternatively, the length of the first and/or second jaw may be shorter than 160 mm, or 140 mm, or 120 mm, or 100 mm. For example, the length of the first and/or second jaw may be in the range of 20-140 mm, or 40-120 mm, or 50-160 mm, or it may be any length within those ranges.

According to at least one example embodiment of the invention, the distance between a male end or a female end when mounted in the first cartridge may than be at least 3 mm, or at least 5 mm, or at least 7 mm, or at least 10 mm. Additionally, or alternatively. The distance between the exit openings may be no longer than 25 mm, or 20 mm, or 15 mm, or 10 mm. For example, the distance between the exit openings may be in the range of 3-25 mm, or 5-20 mm, or 7-15 mm or any distance in those ranges.

According to at least one example embodiment of the invention the first cartridge may comprise exit openings for said male and/or female ends of the wound closers. The distance between the exit openings may than be at least 3 mm, or at least 5 mm, or at least 7 mm, or at least 10 mm. Additionally, or alternatively. The distance between the exit openings may be no longer than 25 mm, or 20 mm, or 15 mm, or 10 mm. For example, the distance between the exit openings may be in the range of 3-25 mm, or 5-20 mm, or 7-15 mm or any distance in those ranges.

According to at least one example embodiment of the invention the male ends and/or the female ends may penetrate the tissue at a distance of at least 3 mm from the edge of the surgical wound. It may for example penetrate the tissue at a distance from the edge of the surgical wound of at least 5 mm, or at least 7 mm, or at least 10 mm. Additionally, or alternatively, the male ends and/or the female ends may penetrate the tissue at a distance from the edge of the surgical wound no longer than 15 mm, or 10 mm, or 7 mm. For example, the male ends and/or the female ends may penetrate the tissue at a distance in the range of 3-10 mm, or 5-15 mm, or 5-10 mm, or any other distance within those ranges.

According to at least one example embodiment of the invention, said cooperating fastening means comprises locking pins and receiving openings each arranged in a respective one of said first and second jaw for locking the position of the first and second jaw relative each other; and/or wherein said second part of said kit of parts further comprises a second handle portion; and wherein the cooperating fastening means is adapted to lock the first and second handle portion to each other; and/or wherein said first jaw is arranged for receiving said first cartridge and/or said second jaw is arranged for receiving said second cartridge.

According to at least one example embodiment of the invention said locking pins may be used as fastening pins for arranging said tissue between said first and second jaw. Stated differently, the fastening pins, if capable of penetrating through the tissue, they may be a part of the cooperating fastening means, i.e. they may be the locking pins of the cooperating fastening means.

According to a third aspect of the invention a method for closing a surgical wound in a tissue with a wound closure device is provided. The method comprises the steps of:
providing said first and second jaw on a respective side of said tissue containing one cartridge each;
actuating the handle to force said male ends and/or said female ends of said plurality of wound closers to exit said first jaw and to penetrate the tissue on one side of the surgical wound where after a respective one of said plurality of tracks in said second cartridge guides said male ends towards a respective female end or said female ends towards a respective male end and into an interlocked state; or
actuating the handle to force said male ends and said female ends of said plurality of wound closers to exit through a respective one of said exit openings in said first jaw, to penetrate the tissue on a respective side of the surgical wound and to enter a respective one of said plurality of tracks where a respective one of said male ends and a respective one of said female ends are guided towards each other and into an interlocked state where said respective one of said male ends and a respective one of said female ends are interlocked with each other.

According to at least one example embodiment of the invention, the step of providing said first and second jaw in said first state comprises a step of attaching first jaw with said second jaw. The first jaw and the second jaw may be attached using the cooperating fastening means.

According to at least one example embodiment of the invention, in the step of actuating the handle, the actuation is performed manually and/or by anon-manual power e.g. compressed air, by a carbonic cartridge or by an electric motor. The non-manual power may be used to facilitate the actuation, especially when said tissue is a thick tissue and a lot of force is needed.

According to at least one example embodiment of the invention, said method further comprises a step of:
tightening of said wound closers by moving one of said jaws away from the tissue.

According to at least one example embodiment of the invention, the second jaw may be detached from the first jaw prior moving it away from the tissue.

Itemized List of Embodiments

A wound closure device for closing a surgical wound in a tissue, wherein said wound closure device comprises a first jaw, a second jaw and a handle;
wherein said first jaw is arranged for receiving a cartridge comprising a plurality of slots for holding wound closers along a longitudinal extension of said, first jaw, wherein each of said plurality of wound closers comprise a male and female end;
wherein said second jaw comprises a plurality of tracks;
wherein said first and second jaws are adapted to be arranged on a respective side of the tissue;
wherein upon one actuation of said handle said first jaw forces said male ends and said female ends to exit said first jaw, to penetrate said tissue on a respective side of said surgical wound and to enter a respective one of said plurality of tracks in said second jaw, wherein said plurality of tracks in said second jaw are arranged to receive said male and female ends and to guide a respective one of said male ends and a respective one of said female ends towards each other and to an interlocked state where said respective one of said male ends and said respective one of said female ends are interlocked with each other.

or wherein upon one actuation of said handle said first jaw forces said male ends to exit said first jaw, to penetrate said tissue on one side of said surgical wound, to enter a respective one of said plurality of tracks in said second jaw, to exit said second jaw, to penetrate the tissue on the opposite side of said surgical wound and to enter said first jaw; and
wherein said plurality of tracks in said second jaw are arranged to receive said male ends and to guide said male to the tissue on said opposite side of said surgical wound; and
wherein said first jaw is arranged to receive said male ends after it has passed said tissue and to guide said male ends to a respective one of said female ends and into an interlocked state where said one of said male ends and one of said female ends are interlocked with each other.

The wound closer device according to item 1, wherein said handle comprises two handle portions wherein at least one of said handle portions is an actuating portion.

The wound closure device surgical stapler according to anyone of the preceding items, wherein said first jaw is arranged underneath or on the internal side of the tissue and wherein said second jaw is arranged, above or on the external side of said tissue.

The wound closure device according to any one of the preceding items, wherein a male end and a female end of the same wound closer, or wherein a male and a female end of two adjacent wound closers are interlocked with each other.

The wound closure device according to anyone of the preceding items wherein the c-c distance between two adjacent slots is 1-10 mm along the longitudinal extension of said first jaw.

The wound closure device according to anyone of the preceding items, wherein said plurality of slots for receiving wound closers is a plurality of slots for receiving clips, staples and/or sutures, e.g. single armed sutures or doubled armed sutures; and/or
wherein said male end of each wound closer comprises one or several protrusions and said female end of each wound closer comprises an opening configured for receiving said male end and wherein said protrusions of said male end are configured to prevent the male end from sliding out of the female end when in said interlocked state.

The wound closure device according to anyone of the preceding items, wherein said tracks in said second jaw is arch-formed and wherein said tracks crosses each other.

The wound closure device according to item 6 when depending on item 5, wherein said tracks are configured to guide said male and female end such that said male end enters through the opening of said female end where said tracks cross each other.

The wound closure device according to anyone of the preceding items, wherein said first and/or said second jaw further comprises at least one fastening pin for partially or fully penetrating the tissue wherein the height of said at least one fastening pin is 1-15 mm The wound closure device according to anyone of the preceding items, wherein the length of the first and/or the second jaw is 20-160 mm, or 40-140 mm, or 50-130 mm; and/or
wherein the distance between a male end and a female end of the same wound closure when mounted in said cartridge is 3-25 mm, or 5-20 mm.

A kit of parts comprising:
  a first part comprising a first handle portion (6a) and a first jaw (2);
  a second part comprising a second jaw (4);
  wherein said first and second parts each comprises cooperating fastening means for locking the first and second jaws to each other;
  wherein said first jaw (2) is arranged for receiving, a cartridge comprising a plurality of slots for holding wound closers (8) along a longitudinal extension of said first jaw (2), wherein each of said plurality of wound closers (8) comprise a male (8b) and female end (8a), and wherein said first jaw (2) comprises exit openings for said male ends (8a) and said female ends (8b) of said wound closure (8);
  wherein said second jaw (4) comprises a plurality of tracks (10);
  wherein said first (2) and second jaws (4) are adapted to be arranged on a respective side of the tissue (100); and
  wherein upon one actuation of said handle portion (6a) said first jaw (2) forces said male ends (8a) and said female ends (8b) to exit through a respective opening in said first jaw (2), to penetrate said tissue (100) on a respective side of a surgical wound (102) and to enter a respective one of said plurality of tracks (10) in said second jaw (4), wherein said plurality of tracks (10) in said second jaw (4) are arranged to receive said male (8a) and female ends (8b) and to guide a respective one of said male ends (8a) and a respective one of said female ends (8b) towards each other and to an interlocked state where said respective one of said male ends (8a) and said respective one of said female ends (8a) are interlocked with each other,
  wherein the first and second part when mounted using the cooperating fastening means forms a wound closure device.

The kit of parts according to item 11, wherein said cooperating fastening means comprises locking pins and receiving openings each arranged in a respective one of said first and second jaw for locking the position of the first and second jaw relative each other; and/or wherein said second part further comprises a second handle portion; and wherein the cooperating fastening means is adapted to lock the first and second handle portion to each other.

A method for closing a surgical wound in a tissue with a wound closure device according any of items 1-12, wherein said method comprises the steps of:
  providing said first and second jaw on a respective side of said tissue;
  actuating the handle to force said male ends and/or said female ends of said plurality of wound closers to exit said first jaw and to penetrate the tissue on one side of the surgical wound where after a respective one of said plurality of tracks in said second jaw guides said male ends towards a respective female end or said female ends towards a respective male end and into an interlocked state; or
  actuating the handle to force said male ends and said female ends of said plurality of wound closers to exit through a respective one of said exit openings in said first jaw, to penetrate the tissue on a respective side of the surgical wound and to enter a respective one of said plurality of tracks where a respective one of said male ends and a respective one of said female ends are guided towards each other and into an interlocked state where said respective one of said male ends and a respective one of said female ends are interlocked with each other.

The method according to anyone of items 12-13, wherein in the step of actuating the handle, the actuation is performed manually and/or by a non-manual power e.g. compressed air, by a carbonic cartridge or by an electric motor.

The method according to anyone of items 12-14, wherein said method further comprises a step of:
  tightening of said wound closers by moving one of said jaws away from the tissue.

BRIEF DESCRIPTION OF THE DRAWINGS

The above objects, as well as additional objects, features and advantages of the present invention, will be more fully appreciated by reference to the following illustrative and non-limiting detailed description of embodiments of the present invention, when taken in conjunction with the accompanying drawings, wherein:

FIG. 7 shows a cross-sectional view of the wound closure device of at least one embodiment of the invention;

FIG. 8 shows a cross-sectional view of a portion of the wound closure device of at least one embodiment of the invention;

FIG. 9 shows a perspective view of the wound closure device according, to at least one embodiment of the invention;

FIG. 10 shows a top, a side and a front view of a cartridge for use with a wound closure device according to at least one embodiment of the invention;

FIG. 11 shows a perspective view of the second jaw of the wound closure device of at least one embodiment of the invention;

FIG. 12 shows a cross-sectional view of the wound closure device of at least one embodiment of the invention;

DETAILED DESCRIPTION

In the present detailed description, embodiments of the present invention will be discussed with reference to the accompanying figures. It should be noted that this by no means limits the scope of the invention, which is also applicable in other circumstances for instance with other types or variants of wound closure devices encompassed by the scope of the claims, than the embodiments shown in the appended drawings. Further, that specific features are mentioned in connection to an embodiment of the invention does not mean that those features cannot be used to an advantage together with other embodiments of the invention.

Figure 1:
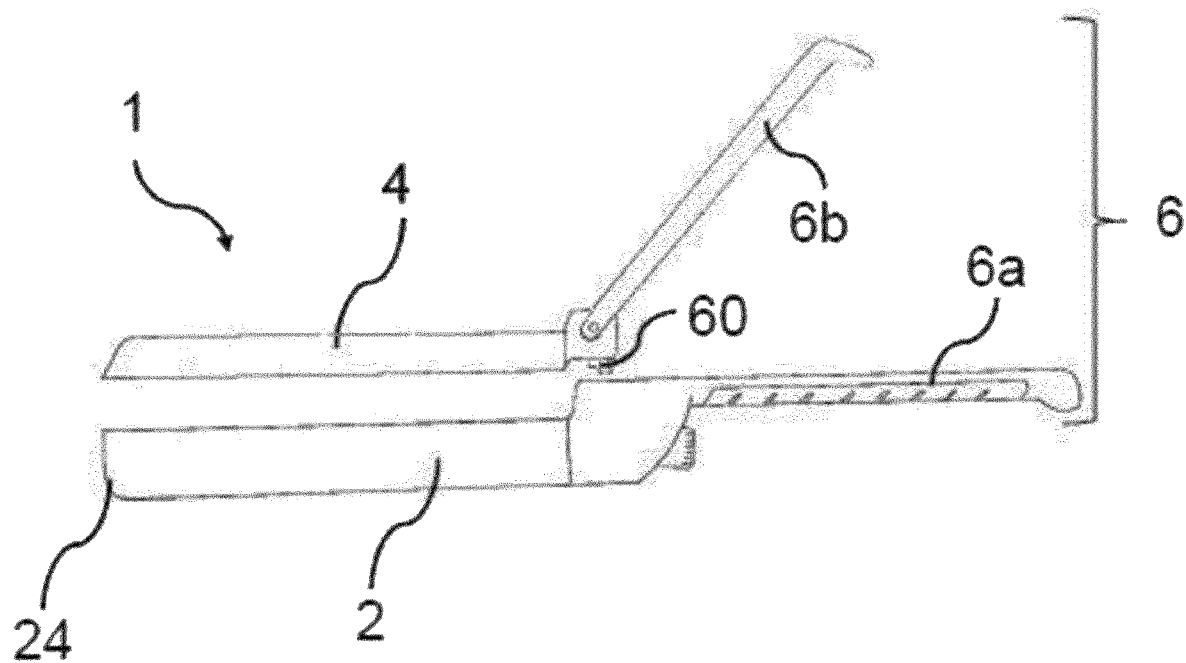
FIG. 1 shows a schematic view of a wound closure device in accordance with at least one embodiment of the invention.

FIG. 1 shows a schematic view of the wound closure device 1. The wound closure device 1 comprises a first jaw 2, a second jaw 4 and a handle 6. The handle 6 comprises a first handle portion 6a and a second handle portion 6b which comprises cooperating fastening means 60. The first jaw 2 comprises an arched leading edge portion 24.

The first jaw 2 is arranged for receiving a first cartridge 12 (not visible in FIG. 1) comprising a plurality of slots 14 for holding wound closers 8 along a longitudinal extension of said first jaw 2. The first 2 and second jaws 4 are adapted to be arranged on a respective side of the tissue, e.g. the muscle fascia.

In FIG. 1 the first handle portion 6a is connected to the first jaw 2 and the second handle portion 6b is connected to the second jaw 4. The first and the second handle portions 6a, b is here disconnected, but may be connected to each other using the cooperating fastening means 60. The first and the second handle portion 6a, b may be connected such that the first and the second jaw is provided at a certain distance from each other and on a respective side of the tissue, e.g. the muscle fascia. The second handle portion 6b is here the actuation portion. Pushing the second handle portion 6b towards the first handle portion 6a is the single actuation upon which the wound closers 8 penetrates the tissue optionally including that the second handle portion is returned to the starting position for example by being biased e.g. by means of spring action, i.e. a spring is compressed when the handle is moved from the starting position to the end position, which spring forces the handle back to the starting position.

Figure 2:
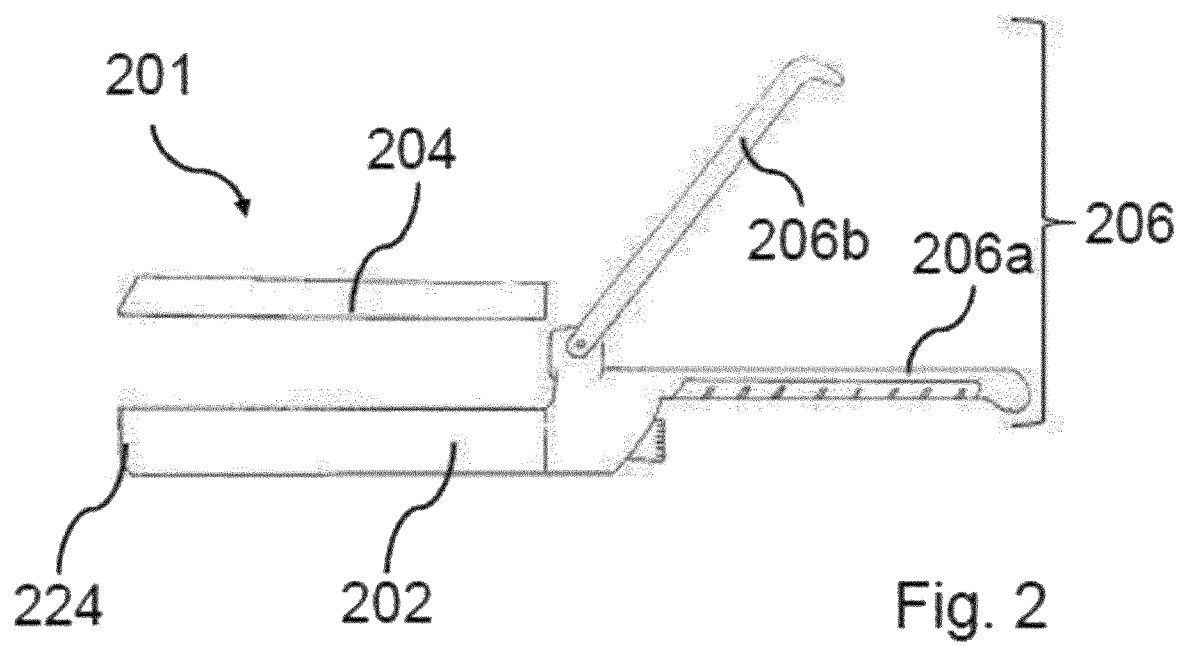
FIG. 2 shows a schematic view of a wound closure device in accordance with at least one embodiment of the invention.

FIG. 2 shows a schematic view of a wound closure device 201. As the wound closure device 201 of FIG. 2 comprises the same features as the wound closure device 1 of FIG. 1 (e.g. the same reference numerals as in FIG. 1, with the addition of the value "200" is used for corresponding features in FIG. 2), focus on the description related to FIG. 2 will be on the differences compared to the wound closure device 1 of FIG. 1.

In FIG. 2 both the first and the second handle portions 206a, b is connected to the first jaw 202. Hence, there is no handle portion connected to the second jaw 204. The first and the second jaw may for example be connected together by the use of cooperating fastening means (not visible in FIG. 2) which may be provided along the first and the second jaws.

Figure 3:
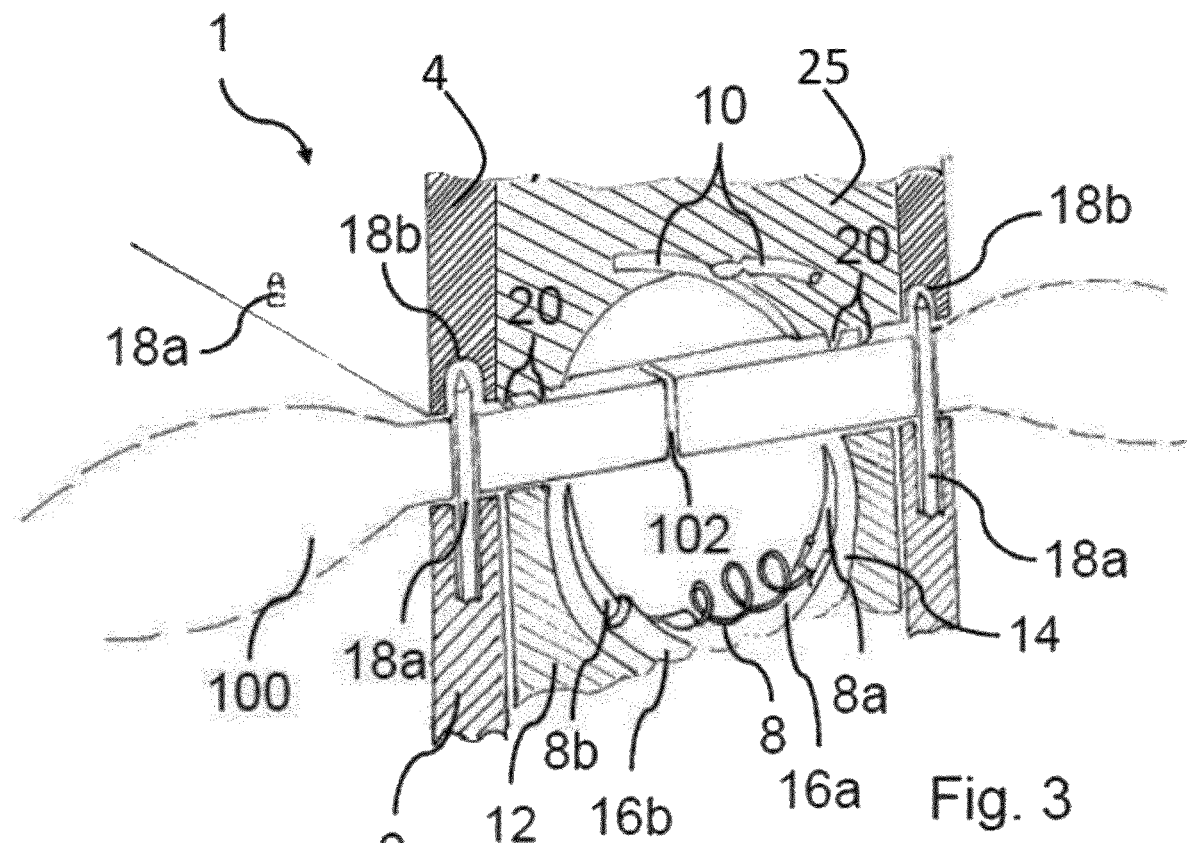
FIG. 3 shows a cross-sectional view of the wound closure device of FIG. 1 when in use in accordance to at least one embodiment of the invention.

FIG. 3. shows a cross-sectional view of the wound closure device 1 in FIG. 1. In FIG. 3 the first cartridge 12 comprising a plurality of slots 14 for holding wound closers 8 is shown. The wound closers 8 comprises a male end 8a and a female end 8b. In FIG. 3 the wound closer 8 is a doubled armed suture. Hence, both the male end 8a and the female end 8b comprises a respective needle. Moreover, in FIG. 3 it is shown that the first jaw 2 further comprises several locking pins 18a of cooperating fastening means and one or several combs, which comprise a plurality of teeth 16a, b which are arranged to push a respective one of the male 8a and female ends 8b upon activation of the handle 6. In FIG. 3, the teeth are curved teeth. The second jaw is provided with a second cartridge 25 in which a plurality of tracks 10 (in FIG. 3, two of these tracks are shown) are formed, alongside receiving openings 18b of cooperating fastening means 18b and fastening pins 20.

The first jaw 2 and second jaw 4 are adapted to be arranged on a respective side of the tissue 100, e.g. the muscle fascia. The fastening pins, and/or the locking pins 18a is arranged to position the tissue 100 in between the first and the second jaw 2, 4 such that the edges of the surgical wound 102 is positioned in close proximity to each other. This is to secure that the male end 8a and the female end 8b penetrates the tissue at a predetermined or desired point.

When in use, upon one actuation of said handle 6 said first jaw 2 forces said male ends 8a and said female ends 8b to exit said first jaw 2, to penetrate said tissue 100 on a respective side of said surgical wound 102 and to enter a respective one of said plurality of tracks 10 in said second jaw 4, wherein said plurality of tracks 10 in said second jaw 4 are arranged to receive said male 8a and female ends 8b and to guide a respective one of said male ends 8a and a respective one of said female ends 8b towards each other and to an interlocked state where said respective one of said male ends 8a and said respective one of said female ends 8b are interlocked with each other.

Figure 4:
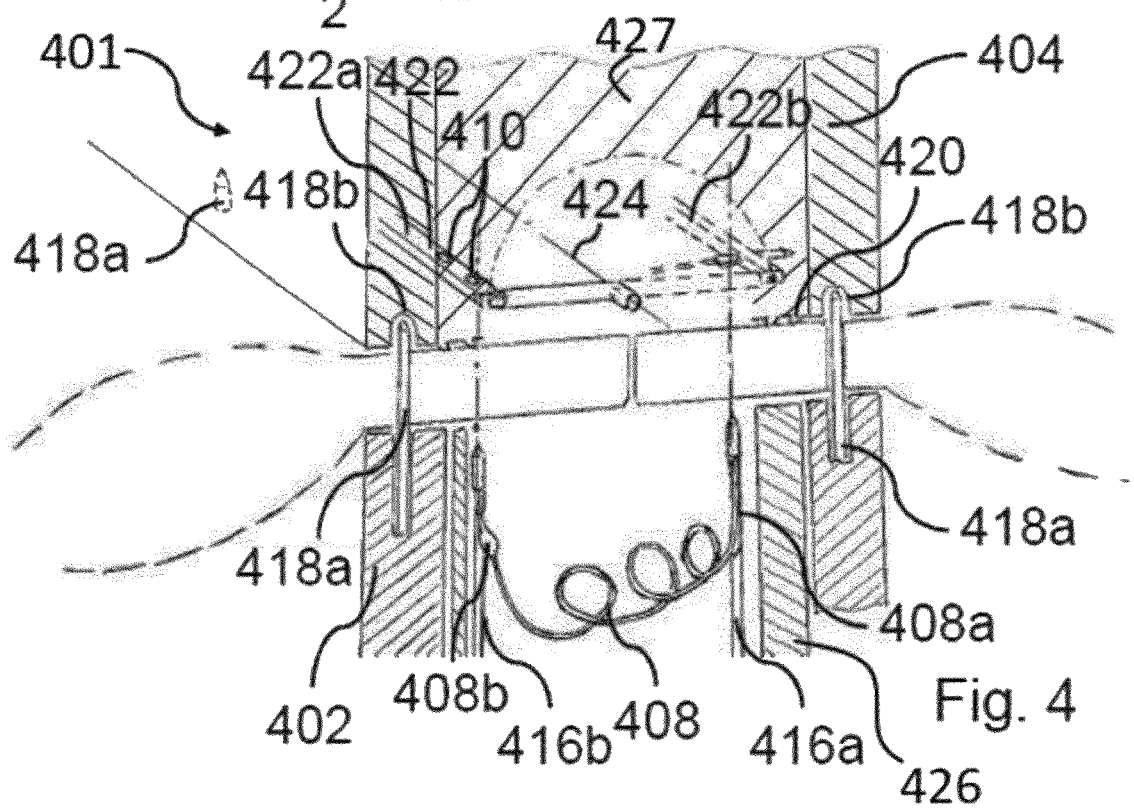
FIG. 4 shows a cross-sectional view of the wound closure device of FIG. 1 when in use in accordance to at least one embodiment of the invention.

FIG. 4 shows a cross-sectional view of a wound closure device 401. As the wound closure device 401 of FIG. 4 comprises the same features as the wound closure device 1 of FIGS. 1 and 3 (e.g. the same reference numerals as in FIG. 1, with the addition of the value "400" is used for corresponding features in FIG. 4), focus on the description related to FIG. 4 will be on the differences compared to the wound closure device 1 of FIGS. 1 and 3.

The first jaw 402 of the wound closure device 401 is provided with a first cartridge 426 that comprises one or several combs comprising straight teeth 416a, b arranged to push a respective one of the female 408b and male ends 408a upon activation of the handle 406. The straight teeth 416b may push the female end 408b in a straight path through the tissue and into the second cartridge 427. The needles enter a respective track 410 in the rod 422 when it is in its first state 422a. The rod 422 subsequently rotates both around the axis 424 and around its own axis into a second state 422b. By this rotation, the female ends 408b is aligned over the male end 408a. The straight teeth 416a subsequently pushes the male ends 408a through the tissue and a through a respective opening of the female end 408b and thus into an interlocked state.

Figure 5:
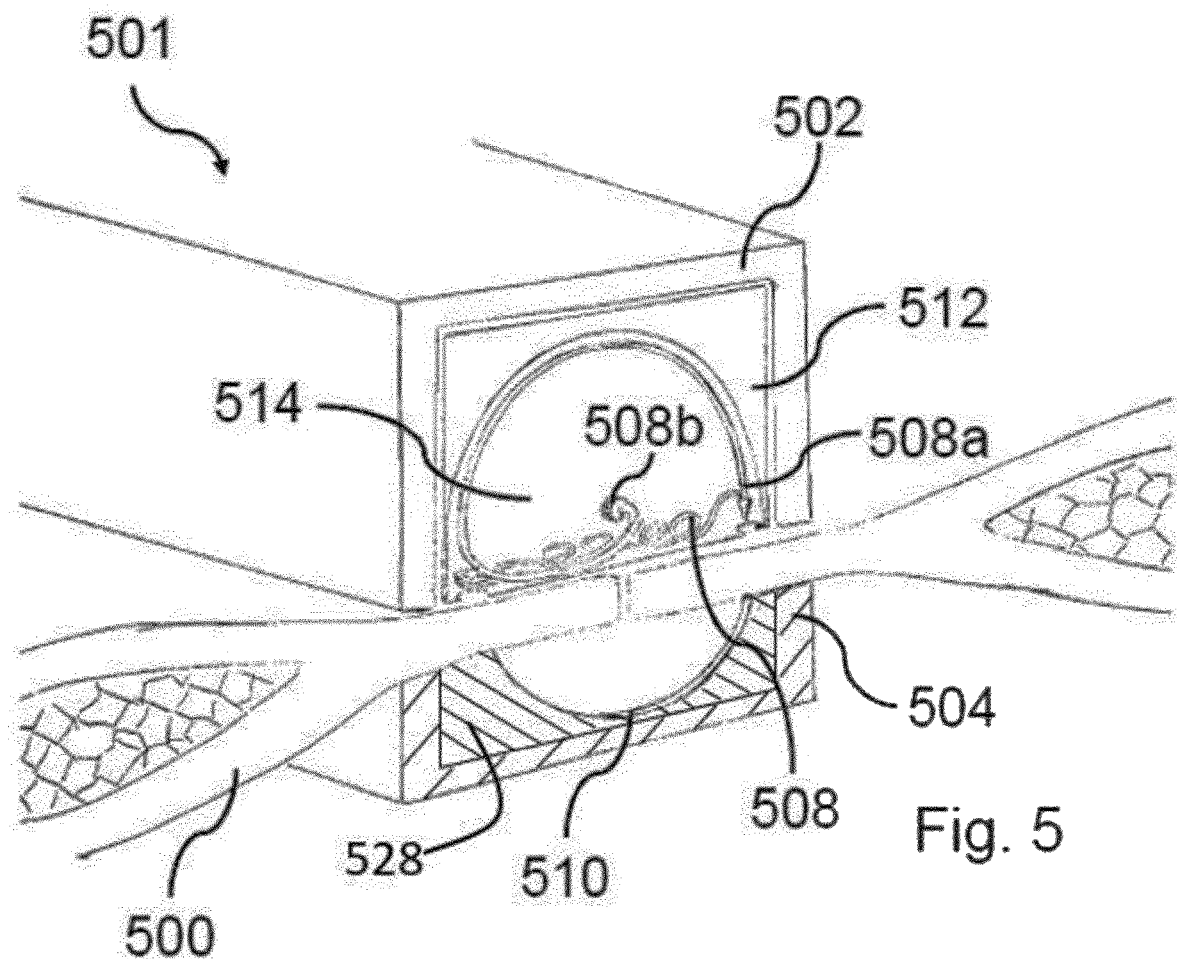
FIG. 5 shows a wound closure device when in use in accordance with at least one embodiment of the invention.

FIG. 5 shows a cross-sectional view of a wound closure device 501. The wound closure device 501 comprises a first jaw 502, a second jaw 504 and a handle (not visible in FIG. 5). The first jaw 502 is provided with a first cartridge 512 comprising a plurality of slots 514 for holding wound closers 508 along a longitudinal extension of said first jaw 502. The wound closers 508 comprises a male end 508a and a female end 508b. In FIG. 5, the wound closers 508 is single-armed sutures. Hence, only the male end 508a comprises a needle which is pushed through the tissue upon actuation of the handle. The second jaw 504 is provided with a second cartridge 528 that comprises a plurality of tracks 510. The first 502 and second jaws 504 are adapted to be arranged on a respective side of the tissue 500, e.g. the muscle fascia. The first jaw 502 is further arranged to receive said male ends 508a after it has passed said tissue 510 and to guide said male ends 508a to a respective one of said female ends 508b and into an interlocked state where said one of said male ends 508a and one of said female ends 508b are interlocked with each other. The plurality of tracks 510 in said second cartridge 528 are arranged to receive said male ends 508a and to guide said male end 508a to the tissue 500 on said opposite side of said surgical wound.

When in use, upon one actuation of the handle said first jaw 502 forces the male ends 508a to exit said first jaw 502, to penetrate said tissue 500 on one side of said surgical wound, to enter a respective one of said plurality 510 of tracks 510 in said second jaw 504, to exit said second jaw 504, to penetrate the tissue 500 on the opposite side of said surgical wound and to enter said first jaw 502.

Figure 6:
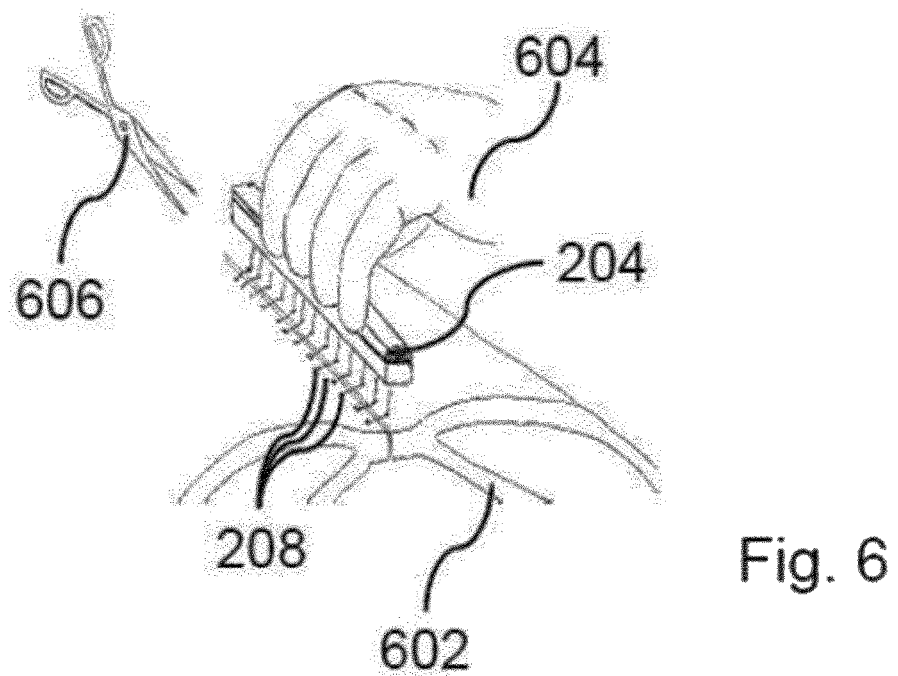
FIG. 6 shows the wound closers being tightened in accordance with at least one embodiment of the invention.

FIG. 6 shows how the second jaw 204 of wound closure device 201 is used to simultaneously tighten the wound closers 208. The wound closers are tightened by moving the second jaw 204 away from the tissue 602 by hand 604. After tightening the wound closures 208, the second jaw 204 is released from the wound closures 208 by the use of a cutting device such as pair of scissors 606. The cutting device could also be integrated in the second jaw.

FIGS. 7-11 show the wound closure device according to at least one exemplary embodiment of the present invention. To prepare the instrument for activation, the first jaw 702 and second jaw 704 are loaded with their respective cartridges; the first jaw with its first cartridge 712 (as can be seen in FIG. 9) and the second jaw 704 with its second cartridge 725, displayed in FIG. 11. Both cartridges 712, 725 are loaded by the same principle shown in FIG. 9, i.e. by moving the cartridges towards the guiding tracks for the cartridge, with the second jaw 704 having substantially identical guiding tracks as the first jaw 702. The cartridges are then held in place by e.g. fastening means 1039 mounted on the cartridges (seen in FIG. 9 and FIG. 10) that connects the cartridges to the respective jaws. To remove the cartridges, these fasteners 1039 are loosened by e.g. releasing a latch on the instrument.

Upon activation of the instrument, a power or an input momentum from the tool will turn the rotational shaft 838 (seen in FIG. 10) which in turn, through its connection to the disk 735a, will turn 735a as well. The input momentum spins the disk 735a around its centre axis, which will rotate its connected disk 735b accordingly. When said momentum is rotating 735a and 735b, be it clockwise or counter-clockwise, the disks 735a and 735b consequentially moves the transfer shaft 736 that is connected between the disks 735a and 735b. The transfer shaft 736 then transfers said rotational motion to a connection joint 732 that connects the needle support arms 716a and 716b, the transfer shaft 736 and the guiding pin 730, while allowing for a rotational motion around the centre axis of said connection. Consequentially, the rotational motion transferred by the transfer shaft 736 moves the connection joint towards or away from the tissue 100, in a direction perpendicular to said tissue. Because the guiding pin 730 that is connected to the connection joint 732 strictly moves in the guiding tracks 731, the guiding pin 730, and the connection joint 732 and all joints connected follow the same movement consequentially. The motion of said connection joint 732 and said guiding pin 730 in said guiding tacks 731 will move the needle support arms 716a and 716b when said needle support arms 716a and 716b is in contact with the four countering pins 734, two on each of the guiding tracks 731, with one mounted on each side of the needle support arms 716a and 716b in the travelling direction of the connection joint 732. The countering pins 734 will move the needle support arms 716a and 716b, and consequentially also the male 708a and female end 708b needles, towards or away from the tissue 100 depending on the direction of the motion of the connection joint. This is possible due to the guiding pin 730 and the transfer shaft 736 not being hindered by the countering pins 734 which lets the guiding pin 730 and the transfer shaft 736 continue its motion as per the guiding tracks 731. When the connection joint 732 is moving away from the tissue 100, the needle support arms 16a and 16b will be pushed against the set of countering pins 734 farthest away from the tissue 100 on the guiding tracks 731, forcing the needle support arms 716a and 716b and consequentially the male 708a and female 708b end needles towards the tissue 100. This said motion forces the male 708a and female 708b end needles to penetrate the tissue 100 through an opening in the first cartridge 712 and enter the opening in the second cartridge allowing for the needle support arms 716a and 716b along with the male 708a and female 708b end needles to move towards the arch-formed tracks 710. Due to a difference in needle length between the male 708a and female 708b end needles, with the female end 708b being longer, the female end needle 708b will enter the arch-formed tracks 710 first, followed by the male end needle 708a. This sequential movement of the male 708a and female 708b end needles will allow the male end 708a to enter the opening 737 in the suturing thread 708, allowing for the thread 708 to create a connected loop through the tissue 100. The needles will reach the end of the arch-formed tracks 710 and the needle locks 729b will interlock with the needle notches 729a.

This interlocking is implemented to allow the male 708a and female 708b needle ends to eject from the needle support arms 716a and 716b by the continuous momentum of the disks 735a and 735b and consequentially the movement retracting the needle support arms 16a and 16b once the connecting point of the transfer shaft 736 to the disks 735a and 735b, as well as the disks 735a and 735b themselves have completed half a rotation from their original position. As the needle support arms 716a and 716b retract by said continuous momentum, the support arms 716a and 716b will retract through the tissue and reach their starting position in the first cartridge 712 whilst the suture 708 will stay connected to the male 708a and female 708b end needles in the second cartridge 725 when the disks 735a and 735b as well as the connecting point of the transfer shaft 736 connected to said disks have completed one whole rotation.

To repeat this process for a plurality of suturing mechanisms, the disk 735b of a first suturing mechanism can be connected to the disk 735a of a following suture mechanism, longitudinally across the first cartridge 712 and the first jaw 702. The disk 735b of said first suturing mechanism and the disk 735a of said following suture mechanism can be connected so that the transfer shafts 736 of the two mechanisms are in the same starting position on the disks 735a and 735b of the two suture mechanisms, allowing for the two mechanisms to produce sutures simultaneously, or at by placing the disk 735b of the first suturing mechanism at an angle in relation to the disk 735a, resulting in different starting positions of the transfer shafts 736 between the two suturing mechanisms, allowing for the two mechanisms to produce sutures sequentially. This can be repeated once again to produce a plurality of sutures through one full rotation of the first disk 735a of the suturing mechanism rotated by the input momentum from the rotational shaft 838 the centre axis of the disk 735a produced by the instrument. The result of the connected mechanisms along the length of the cartridge 712 can be seen in FIG. 10.

To tighten the sutures, the second cartridge 725 is moved (with or without the second jaw 704) perpendicularly away from the tissue 100 as per FIG. 6. In this movement, the loop created in the suture 708 will be tightened and remain tight due to the suture protuberances 840 the thread opening 737 only allowing movement one direction, therefore only allowing tightening of the suture 708. The suture 708 can then be cut off, separating them from the needles and consequentially the second cartridge as per FIG. 6.

Figure 15:
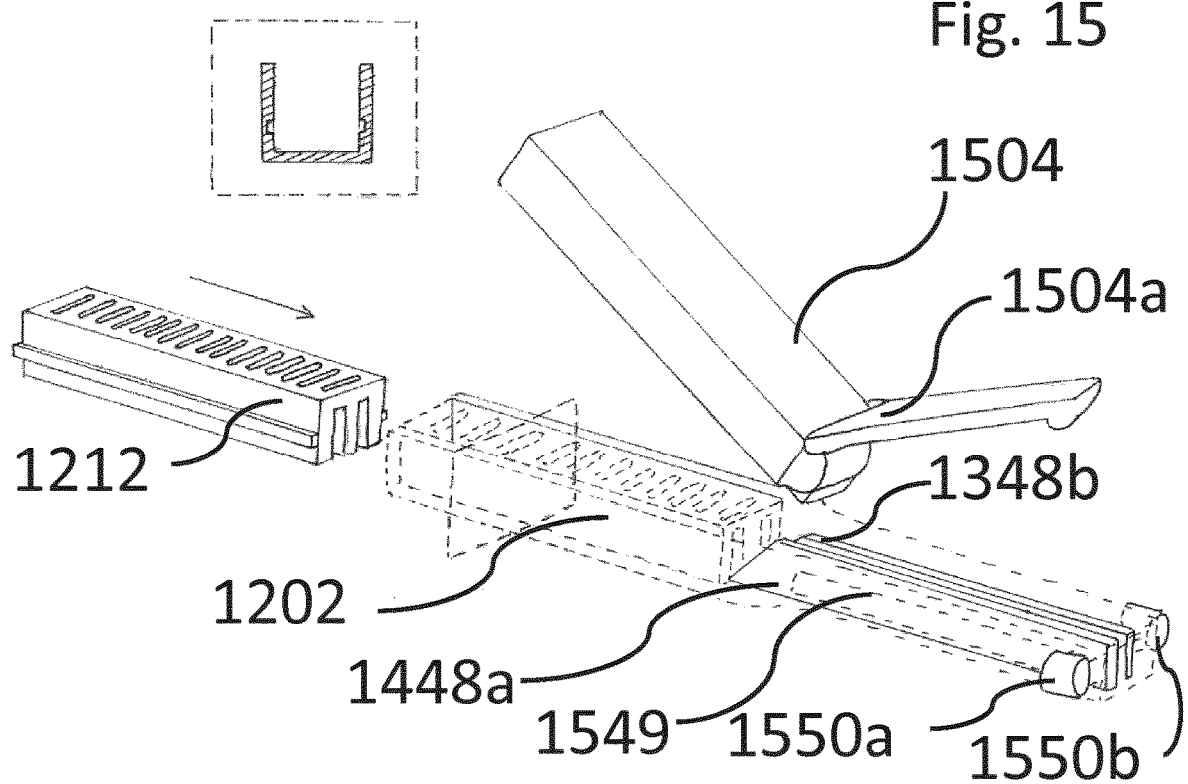
FIG. 15 shows a perspective view of the wound closure device according to at least one embodiment of the invention.
Figure 16:
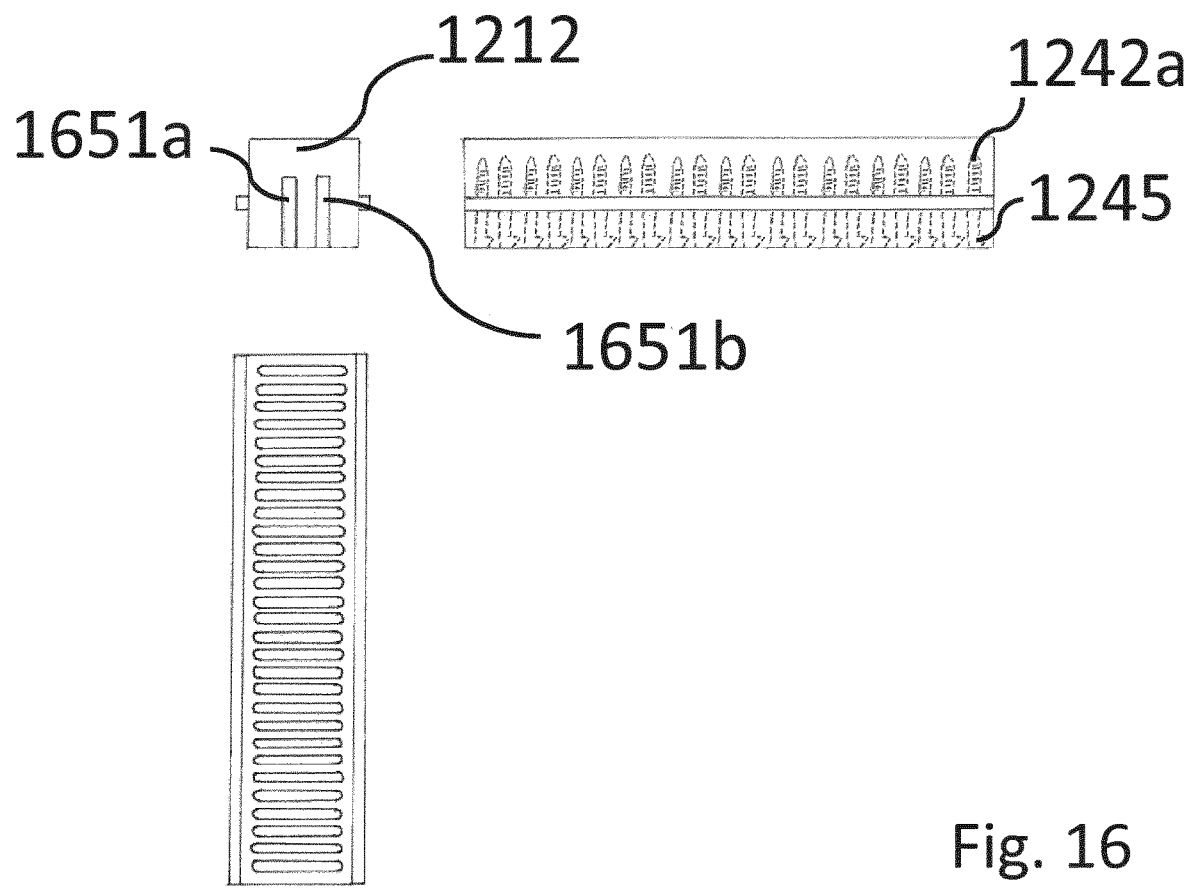
FIG. 16 shows a top, a side and a front view of a cartridge for use with a wound closure device according to at least one embodiment of the invention.
Figure 17:
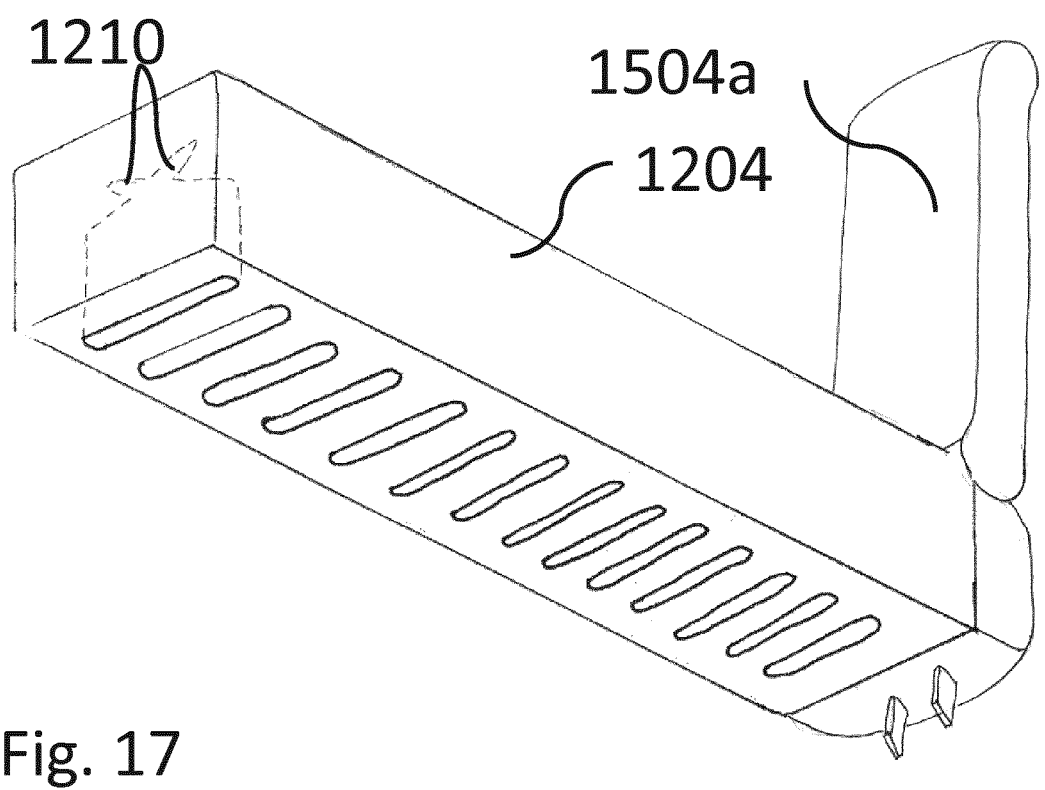
FIG. 17 shows a perspective view of the second jaw of the wound closure device of at least one embodiment of the invention.

FIGS. 12-17 show the wound closure device according to at least one example embodiment. To prepare for activation, the instrument is loaded by connecting the cartridge 1212 to the first jaw 1202 as can be seen in FIG. 15. The cartridge 1212 is guided in place by its connecting rails that are guided in the first jaw 1202 through the cut-outs as can be seen in the FIG. 15. The second jaw 1204 does not contain a separate cartridge, as the jaw itself has the guiding tracks 1210, as can be seen in FIG. 17.

To activate the tools once the first jaw 1202 and the second jaw 1204 is connected and the tissue 100 is in place, the rail button 1550b connected to the push rail 1348b is moved longitudinally away from its starting position, towards the cartridge 1212 that, at this stage, is placed and connected to in the first jaw 1202, as is represented by the dashed line in FIG. 15. The rail button 1550b is allowed this movement by the side openings 1549 in the first jaw 1202. Upon activation and forcing the rail button 1550b and consequentially the push rail 1348b towards and into the cartridge 1212, the process of wound closure begins.

Figure 13:
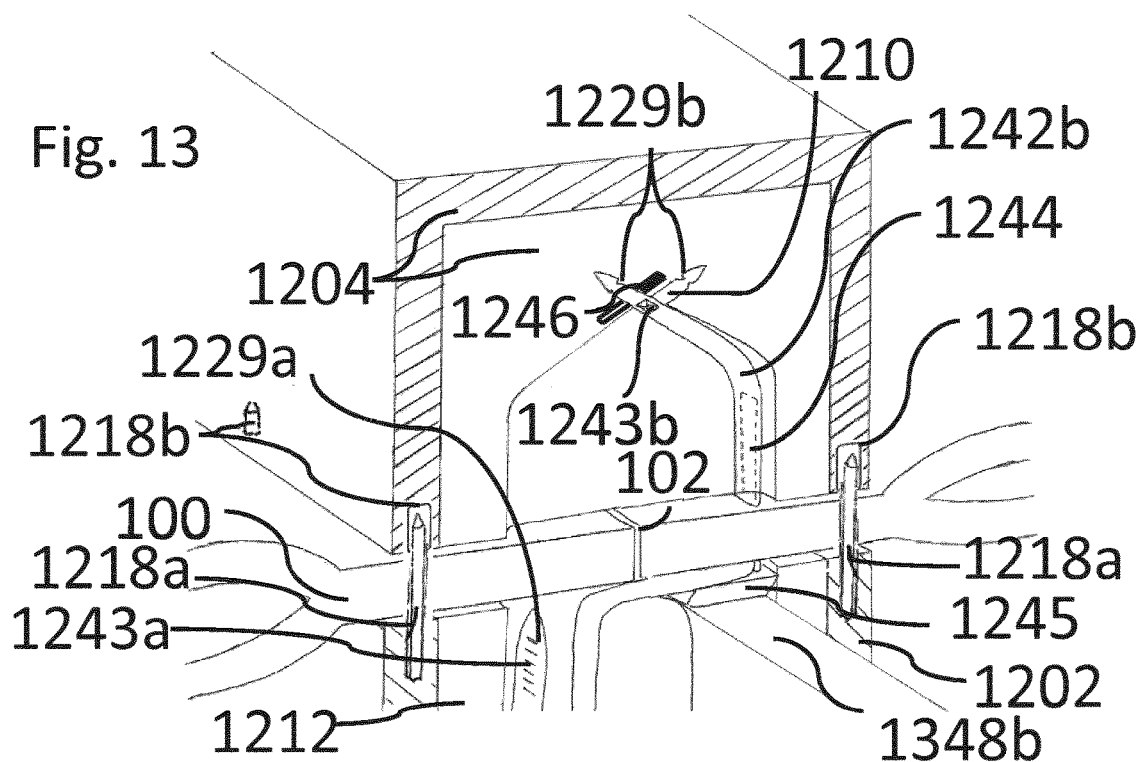
FIG. 13 shows a cross-sectional view of a portion of the wound closure device of at least one embodiment of the invention.
Figure 14:
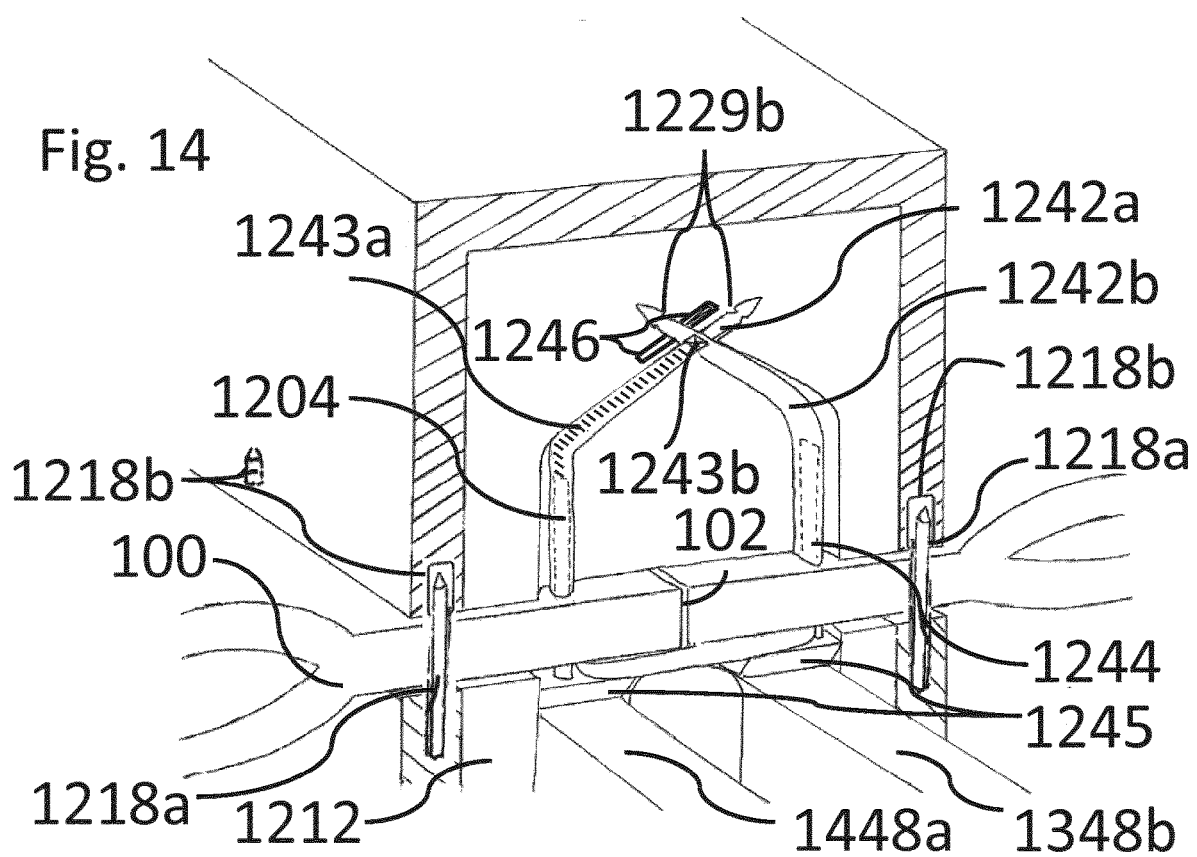
FIG. 14 shows a cross-sectional view of a portion of the wound closure device of at least one embodiment of the invention.

The view of the internal mechanisms of cartridge 1212 can be seen in FIG. 12. FIG. 12 shows the mechanisms before the push rail 1348b is forced into the cartridge 1212. When the push rail 1348b is forced into the said cartridge (through the opening 1651b as seen in FIG. 16), the pointed tip of the push rail 1348b and the matching shape of the mounting frame 1245 seen in FIG. 12 is forced to upwards, away from its starting position, against the top of the cartridge along the frame guide path 1247. This said movement in turn forces the mounting pin 1244 connected to said mounting frame and consequentially also the female end of the self-interlocking fastening element 1242b towards the top of the cartridge and towards the tissue 100. The mounting pin 1244 is connected to the female end of the self-interlocking fastening element 1242b by a pocket in said end of the self-interlocking mechanism, allowing the mounting pin to provide support while being able to be removed from the female end of the self-interlocking fastening element 1242b when the push rail is retracted to its starting position. Said self-interlocking fastening element then penetrates the tissue 100 with its female end 1242b and is forced into its locking track 1210, as can be seen in FIG. 13, once the pointed end of push rail 1348b has pushed the mounting frame 1245 to sit the top of the push rail 1348b. The female end of the self-interlocking fastening element 1242b is kept in place in its locking track 1210 by the protruding locking mechanisms 1229b and the notches 1229a in the tip of the female end of said self-interlocking fastening element 1242b.

To connect the male 1242a and female 1242b ends of the self-interlocking fastening element, the second rail button 1550a is forced towards the cartridge 1212, the same way the rail button 15501) is moved. This repeats the process of forcing the push rail 1448a towards and into the cartridge through the opening 1651a, forcing the mounting frame 1245 towards the top of the cartridge, in turn forcing the mounting pin 1244 and the male end of the self-interlocking fastening element 1242a towards and through the tissue, and finally through the tension-adjusting opening 1243b in the female end of the self-interlocking fastening element, into its locking track 1210. Similarly, to the female end of the self-interlocking fastening element, the male end of said self-interlocking fastening element is kept in place by the locking mechanisms 1229b in its locking track 1210.

Once the push rails 1348b and 1448a are forced to the far end of the guiding paths 1549 (FIG. 15) and all the fastening elements are interlocked all through the length of the cartridge 1212, the push buttons 1550a and 1550b and consequentially the push rails 1448b and 1348a can be retracted to their starting positions. This retracts the mounting frames 1245 and consequentially the connected mounting pins 1244 down to their starting position in the cartridge 1212 as seen in FIG. 12.

To finish the process, the handle 1504a can be pushed down which moves a cutting blade 1246 connected to the handle and that runs all through the length of the second jaw, that cuts the tip of the female end of the self-interlocking fastening element 1242b, loosening the remaining of the female end that is still connected to the male end of the self-interlocking fastening element 1242a through the opening 1243b. Once the handle 1504a of the second jaw 1204 have been pushed, the second jaw 1204 can be removed from its connection with the first jaw 1202. By moving the second jaw 1204 away from the tissue, in the direction normal to the surface of the tissue, the self-interlocked fastening elements can be tightened in the same fashion displayed in FIG. 6.

The skilled person realizes that a number of modifications of the embodiments described herein are possible without departing from the scope of the invention, which is defined in the appended claims. For instance, the wound closure device may be used with other types of wound closers than what is described above.

The invention claimed is:

1. A wound closure device for closing a surgical wound in a tissue, wherein the wound closure device comprises a first jaw, a second jaw and a handle;
    wherein the first jaw is arranged for receiving a first cartridge, and wherein the first jaw is provided with the first cartridge,
    wherein the first cartridge comprises a plurality of slots holding wound closers, the slots being distributed along a longitudinal extension of the first cartridge, and wherein each of the plurality of wound closers comprise a male and female end;
    wherein the second jaw is provided with a plurality of tracks;
    wherein the tracks are curved and/or linear and wherein the tracks cross each other;
    wherein the first and second jaws are adapted to be arranged on a respective side of the tissue;
    wherein the wound closure device further comprises power transfer means operatively coupled to the handle for transferring power to the first cartridge;
    wherein the first cartridge further comprises:
    connection means for connecting the first cartridge to a power receiving means configured to receive power from the power transfer means; and
    actuation means operatively coupled to the power receiving means and configured to force the male ends and the female ends to exit the first cartridge and to penetrate the tissue on a respective side of the surgical wound
    wherein upon one actuation of the handle, via the actuation means, is configured to force the first jaw the male ends and the female ends to exit the first cartridge, and to penetrate the tissue on a respective side of the surgical wound and to enter a respective one of the plurality of tracks, wherein the plurality of tracks are arranged to receive the male and female ends and to guide a respective one of the male ends and a respective one of the female ends of the same wound closer towards each other, and to an interlocked state where the respective one of the male ends and the respective one of the female ends of the same wound closer are interlocked with each other.

2. The wound closure device according to claim 1, wherein the tracks are formed in the second jaw.

3. The wound closure device according to claim 1, wherein the second jaw is provided with a second cartridge, and wherein the tracks are formed in the second cartridge.

4. The wound closure device according to claim 1, wherein the handle comprises two handle portions wherein at least one of the handle portions is an actuating portion.

5. The wound closure device according to claim 1 wherein a center-to-center distance between two adjacent slots is 1-10 mm along the longitudinal extension of the first jaw.

6. The wound closure device according to claim 1, wherein the plurality of wound closers are adjustable, partly flexible, self-locking, and/or self-penetrating.

7. The wound closure device according to claim 1, wherein the male end of each wound closer comprises one or several protrusions and the female end of each wound closer comprises an opening configured for receiving the male end, and wherein the protrusions of the male end are configured to prevent the male end from sliding out of the female end when in the interlocked state.

8. The wound closure device according to claim 1, wherein the tracks are configured to guide the male and female end such that the male end enters through the opening of the female end where the tracks cross each other.

9. The wound closure device according to claim 1, wherein the first and/or the second jaw further comprises at least one fastening pin for partially or fully penetrating the tissue wherein the height of the at least one fastening pin is 1-15 mm.

10. The wound closure device according to claim 1, wherein the length of the first and/or the second jaw is 20-160 mm.

11. The wound closure device according to claim 1, wherein the length of the first and/or the second jaw is 40-140 mm.

12. The wound closure device according to claim 1, wherein the length of the first and/or the second jaw is 50-130 mm.

13. The wound closure device according to claim 1, wherein the distance between a male end and a female end of the same wound closer when mounted in the first cartridge is 3-35 mm.

14. The wound closure device according to claim 1, wherein the distance between a male end and a female end of the same wound closer when mounted in the first cartridge is 3-25 mm.

15. The wound closure device according to claim 1, wherein the distance between a male end and a female end of the same wound closer when mounted in the first cartridge is 5-20 mm.

16. The wound closure device according to claim 1, wherein the length of the first and/or the second jaw is 20-160 mm and the distance between a male end and a female end of the same wound closer when mounted in the first cartridge is 3-35 mm.

* * * * *